United States Patent
Parlante

(10) Patent No.: US 9,700,454 B2
(45) Date of Patent: Jul. 11, 2017

(54) ERECTILE DYSFUNCTION BAND

(71) Applicant: Joseph Parlante, Washington, DC (US)

(72) Inventor: Joseph Parlante, Washington, DC (US)

(*) Notice: Subject to any disclaimer, the term of this patent is extended or adjusted under 35 U.S.C. 154(b) by 151 days.

(21) Appl. No.: 14/674,029

(22) Filed: Mar. 31, 2015

(65) Prior Publication Data
US 2015/0290023 A1 Oct. 15, 2015

Related U.S. Application Data

(60) Provisional application No. 61/978,506, filed on Apr. 11, 2014.

(51) Int. Cl.
*A61F 5/41* (2006.01)

(52) U.S. Cl.
CPC .......... *A61F 5/41* (2013.01); *A61F 2005/414* (2013.01)

(58) Field of Classification Search
CPC . A61F 5/41; A61F 2005/412; A61F 2005/414
See application file for complete search history.

(56) References Cited

U.S. PATENT DOCUMENTS

| | | | |
|---|---|---|---|
| 4,203,432 A | 5/1980 | Koch | |
| 5,855,548 A * | 1/1999 | Place | A61F 5/41 128/885 |
| 5,873,813 A | 2/1999 | Weiss | |
| 6,306,080 B1 | 10/2001 | Mitchell et al. | |
| 7,390,297 B2 | 6/2008 | Ford | |
| 7,674,225 B2 | 3/2010 | Shelyakov et al. | |
| 2005/0101835 A1* | 5/2005 | Magee | A61F 5/41 600/38 |
| 2013/0303342 A1 | 11/2013 | Mandell | |

* cited by examiner

*Primary Examiner* — Christine H Matthews
(74) *Attorney, Agent, or Firm* — Global Intellectual Property Agency, LLC; Daniel Boudwin

(57) ABSTRACT

A device for alleviating erectile dysfunction includes a unitary tube having a flat top portion, a first leg, and a second leg. The first leg and the second leg extend from opposing ends of the flat top portion. The flat top portion is configured to lay across a base of a penis. The first leg and the second extend inwardly to a constriction region to form a receiving cavity. The receiving cavity is configured to receive the penis. The first leg and the second leg extend outwardly from the constriction region to form handle portions. An elastic loop portion extends from a distal end of the second leg. The elastic loop portion is configured to constrict the two leg portions at the constriction region.

3 Claims, 2 Drawing Sheets

ERECTILE DYSFUNCTION BAND

CROSS REFERENCE TO RELATED APPLICATION

This application claims the benefit of U.S. Provisional Application No. 61/978,506 filed on Apr. 11, 2014. The above identified patent application is herein incorporated by reference in its entirety to provide continuity of disclosure.

FIELD OF THE INVENTION

The present invention generally relates to relieving erectile dysfunction. More particularly, the present invention relates to a device that applies pressure to the dorsal veins of a penis to relieve erectile dysfunction.

BACKGROUND OF THE INVENTION

Erectile dysfunction (ED) is a medical condition for which millions of American men seek treatment every year. According to the National Institutes of Health, between 15 million and 30 million men suffer from ED, which is loosely defined as the repeated inability to get or keep an erection firm enough for sexual intercourse. The wide range for the estimate of the numbering of individuals suffering from ED stems from the rather vague definition, as ED can be a total inability to achieve erection, an inconsistent ability to do so, or a tendency to sustain only brief erections. Under normal conditions, an erection is achieved when blood flows into the penis and fills the corpora cavernosa, large cylindrical tissue structures which run the length of the penis and, when filled with blood, cause the penis to become rigid and erect. The corpora cavernosa are surrounded by the tunicae, elastic sheaths which expand with the corpora cavernosa and apply pressure to the veins which would normally drain the blood from the corpora cavernosa. In some cases, the cause of ED is linked to an inability to provide sufficient blood flow to the penis to fill the corpora cavernosa and achieve an erection. In other situations, the tunicae are not able to press against the blood-draining veins with sufficient force to maintain the erection.

While many of those afflicted with ED are older, with approximately half of the sufferers believed to be over the age of 65, ED is a condition which can affect men at any age, as the causes of ED are extremely varied. Damage to nerves, arteries, smooth muscles, and fibrous tissues from disease is the most common cause of ED. These diseases, such as diabetes, multiple sclerosis, atherosclerosis, and vascular disease, account for about 70 percent of ED cases. In addition, many common medicines including blood pressure drugs, antihistamines, and antidepressants can cause ED. Certain risky lifestyle choices, such as smoking, being overweight, and avoiding exercise, may also contribute to ED. It is also believed that psychological factors, such as stress, anxiety, depression, and fear of sexual failure, cause approximately 10 to 20 percent of ED cases.

Mechanical devices are available for producing and/or maintaining erections. These devices include large, cumbersome vacuum pumps for drawing blood into the penis and restrictors which hold blood in the penis by applying pressure to the subcutaneous veins which drain the penis of blood. Especially for those who suffer from the more mild forms of ED, restrictors are a very popular option. Such restrictors include continuous rigid rings, adjustable straps, or the like. Restrictors are described, for example, in U.S. Pat. No. 5,855,548 (rubber tubing looped around the base of the penis), U.S. Patent Pub. US 2003/0009082 (an adjustable gold ring through which the penis is inserted), U.S. Patent Pub. US 2004/0242957 (an adjustable rigid band encircling a portion of the base of the penis), and U.S. Patent Pub. US 2005/0277907 (joined elastic rings worn around the scrotum and the base of the penis).

These prior art devices have several known drawbacks. Each of these devices addresses the need for restricting blood flow from the penis. The current invention goes beyond the present art to provide a unitary tube having a flat top portion, a first leg, and a second leg that provides a constriction region that can be adjusted according to the preference of a user. The unitary tube is covered in a soft surgical tissue material for comfort, yet has a rigid interior to provide adequate pressure to the base of the penis.

In light of the devices disclosed in the prior art, it is submitted that the present invention substantially diverges in design elements from the prior art and consequently it is clear that there is a need in the art for an improvement to existing devices for increasing blood flow to a penis. In this regard the instant invention substantially fulfills these needs.

SUMMARY OF THE INVENTION

In view of the foregoing disadvantages inherent in the known types of mechanical devices for increasing blood flow to a penis now present in the prior art, the present invention provides a device that applies to pressure to the base of the penis wherein the same can be utilized for providing convenience for the user when having erectile dysfunction.

It is therefore an object of the present invention to provide a new and improved device for relieving erectile dysfunction that has all of the advantages of the prior art and none of the disadvantages.

It is another an object of the present invention to provide a device for alleviating erectile dysfunction. The device includes a unitary tube comprising a flat top portion, a first leg, and a second leg. The first leg and the second leg extend from opposing ends of the flat top portion. The flat top portion is configured to lay across a base of a penis. The flat top portion potion applies pressure to the dorsal veins of the penis.

It is yet another object of the present invention to provide a receiving cavity configured to receive the penis. The first leg and the second leg of unitary tube extend inwardly to a constriction region to form the receiving cavity.

Another aspect of the present invention is provide at least two handle portions. The first leg and the second leg extend outwardly from the constriction region to form the at least two handle portions.

Yet another aspect of the present invention is to provide an elastic loop portion extending from a distal end of the second leg. The elastic loop portion is configured to constrict the two leg portions at the constriction region. The elastic loop portion can be twisted to provide various levels of constriction.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
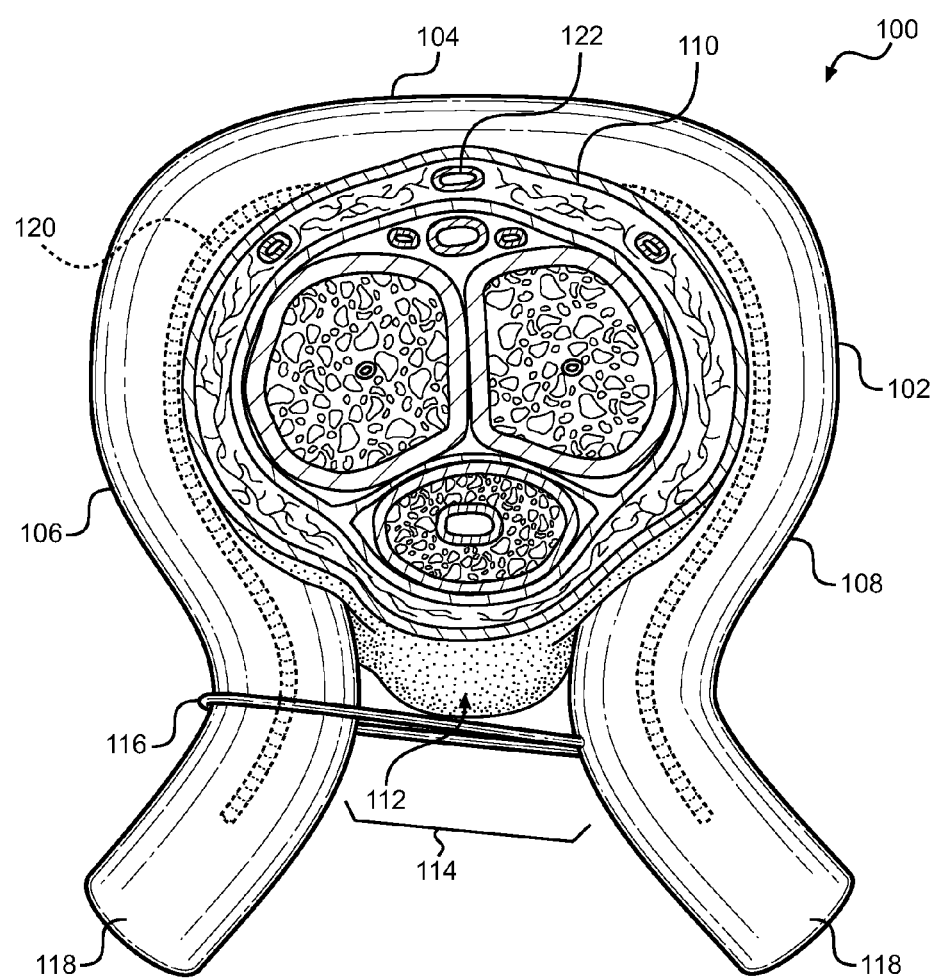
FIG. 1 shows the device constricting blood flow from the penis according to one embodiment of the present invention.

Reference is made herein to the attached drawings. Like reference numerals are used throughout the drawings to depict like or similar elements of the device for alleviating erectile dysfunction. For the purposes of presenting a brief and clear description of the present invention, the preferred embodiment will be discussed as used for an individual suffering from erectile dysfunction. The figures are intended for representative purposes only and should not be considered to be limiting in any respect.

The invention provides a tube band apparatus that can help men who suffer from erectile dysfunction with attaining and maintaining an erection. The invention provides a tube band apparatus that works in conjunction with Kegel exercises. The device provides an inner core area that can be made from ribbed plastic or another suitable material and includes a rigid top area all of which can be covered with a soft surgical tubing material. The band can be placed over the base area of the penis near the scrotum. The device provides a flat top portion that keeps pressure on the dorsal veins of the penis when in use, while the two legs of the device can flex in an open or closed position in order to allow inflow of arterial blood. The structure of the device comprises soft tubing that prevents bruising and thus facilitates comfort for the user. The device allows the user to customize the degree of constriction to the penis thereto.

Referring now to FIG. 1, there is shown the device for constricting blood flow from the penis according to one embodiment of the present invention. The device 100 for alleviating erectile dysfunction includes a unitary tube 102 having a flat top portion 104, a first leg 106, and a second leg 108. The unitary tube 102 comprises a flexible tubing material having a rigid body. The unitary tube 102 includes a soft outer shell material.

The first leg 106 and the second leg 108 extend from opposing ends of the flat top portion 104. The flat top portion 104 is configured to lay across a base of a penis 110. The edges of the flat top portion 104 are rounded to complement the contour of the base of a penis. The flat top portion 104 applies pressure to dorsal veins 122 of the penis 110 when the elastic loop portion 116 constricts the first leg 106 and the second leg 108. The first leg 106 and the second leg 108 extend outwardly from the constriction region 114 to form handle portions 118.

The body of the unitary tube includes a receiving cavity 112. The first leg 106 and the second leg 108 extend inwardly to a constriction region 114 to form the receiving cavity 112. The receiving cavity 112 is configured to receive the penis 110. The unitary tube 102 further comprises an inner core 120 having a ribbed interior. The ribbed interior of the inner core provides additional resistance for constriction. The first leg 106 and the second leg 108 extend inwardly to the constriction region 114 and then outwardly from the constriction region 114, defining an hourglass-like shape.

An elastic loop portion 116 extends from a distal end of the second leg 108. The elastic loop portion 116 is configured to constrict the first leg 106 and the second leg 108 at the constriction region 114. The elastic loop portion 116 can be twisted to provide various levels of constriction. The elastic loop portion 116 may be located on the lower interior area of the first leg 106 or the second leg 108 and is used to secure and tighten the device 100 over the penis 110.

A user can control the amount of constriction via adjusting the degree of tightness of the unitary tube 102. The user can twist the elastic loop portion 116 a number of times in order to reach an appropriate and desired penis constriction level. The user can then engage in Kegel exercises wherein the device 100 can be repeatedly loosened and tightened via the pulsation that occurs as a result of performing Kegel exercises. The repeated Kegel contractions and releases allow for the influx of arterial blood, while the dorsal veins remain compressed by the flat top portion 104 of the device 100, thus aiding with attaining an erection.

Figure 2:
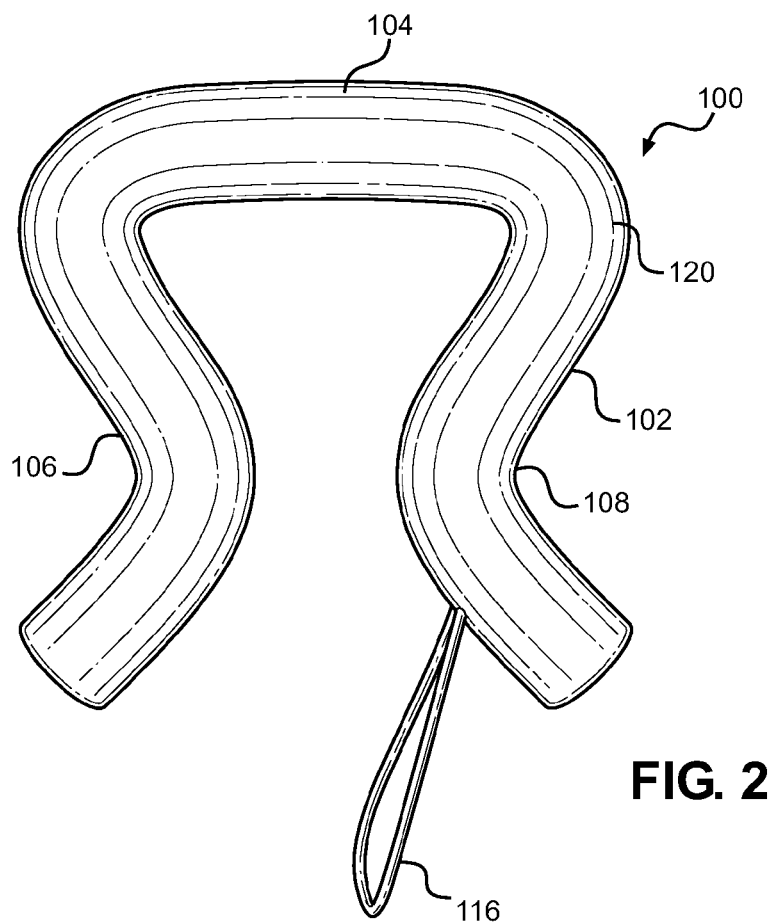
FIG. 2 shows the unitary tube according to one embodiment of the present invention.

Referring now to FIG. 2, there is shown the device for constricting blood flow from a penis according to one embodiment of the present invention. The device 100 comprises an inner core 120 of ribbed plastic and a rigid flat top portion 104 that is covered with soft surgical tubing. The unitary tube 102 is placed over the penis at the base near the scrotum, thereafter an elastic loop portion 116 is wrapped around the proximal and distal ends of the unitary tube 102. The amount of constriction caused by the unitary tube 102 is determined by the amount that the elastic loop portion 116 is wrapped around the first leg 106 and the second leg 108 of the unitary tube 102. A user may perform Kegel exercises to loosen and retighten the unitary tube 102 while the flat top portion 104 compresses the dorsal veins. Repeated Kegel contracts allow for the influx of arterial blood, while the dorsal veins remain compressed by the rigid top portion 104, thus aiding and strengthening erections.

Figure 3:
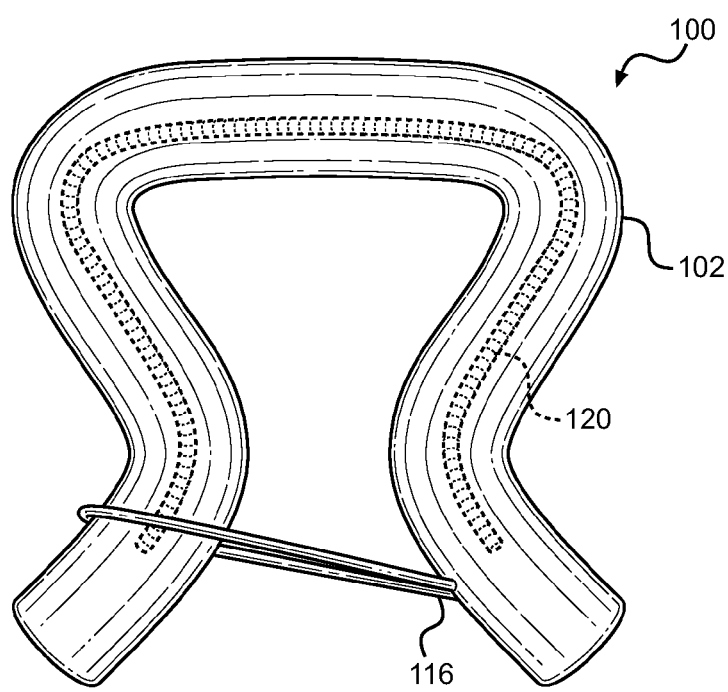
FIG. 3 shows unitary tube according to one embodiment of the present invention.

Referring now to FIG. 3, there is shown the device for constricting blood flow from a penis according to one embodiment of the present invention. There is shown a view of the unitary tube 102 band of the present invention with the elastic loop portion 116 in a closed position. The device 100 provides a unitary tube 102 that can be placed around the base portion of the penis in order to aid the user in attaining an erection, thereby helping to prevent, treat, and correct erectile dysfunction. When the user places the device over top of the penis, the user can then engage in physical and/or psychological stimuli. The device 100 comprises a ribbed internal plastic core 120 that is covered with soft surgical tubing. The attached elastic loop portion 116 located on one leg of the device can be placed around the other leg of the device and the user can adjust the degree of constriction of the device via pulling the legs closer to one another or by releasing the legs to a further distance from one another.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A device for alleviating erectile dysfunction, comprising:
   a rigid unitary tube comprising a flat top portion, a ribbed core extending longitudinally along a length of the unitary tube, a first leg, and a second leg, the unitary tube including a flexible outer material;
   the first leg and the second leg extending symmetrically from opposing ends of the flat top portion, such the first leg and the second leg are equal in length and symmetrical relative to each other about the flat top portion;
   wherein the first leg and the second leg include a proximal end extending radially inwardly forming a constriction region including a receiving cavity; and
   an elastic loop portion affixed to a distal end of the second leg, the elastic loop portion configured to fasten the distal end of the second leg to a distal end of the first leg and constrict the first leg and the second leg relative to each other at the constriction region;
   wherein the distal end of the first leg and the distal end of the second leg extend radially outwardly from the constriction region to form a handle portion.

2. The device of claim 1, wherein the flat top portion potion is adapted to apply pressure to dorsal veins of a penis when the elastic loop portion constricts the first leg and the second leg.

3. The device of claim 1, wherein the elastic loop portion is adjustable around the distal ends of the first and second legs in order to adjust the tightness of the constriction region.

* * * * *